(12) United States Patent
Li et al.

(10) Patent No.: US 11,801,374 B2
(45) Date of Patent: Oct. 31, 2023

(54) METHODS AND SYSTEMS FOR NON-CONTACT CONSTRUCTION OF AN INTERNAL STRUCTURE

(71) Applicant: THE GENERAL HOSPITAL CORPORATION, Boston, MA (US)

(72) Inventors: Li Li, Quincy, MA (US); Guillermo J. Tearney, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 371 days.

(21) Appl. No.: 16/329,862

(22) PCT Filed: Sep. 1, 2017

(86) PCT No.: PCT/US2017/049850
§ 371 (c)(1),
(2) Date: Mar. 1, 2019

(87) PCT Pub. No.: WO2018/045284
PCT Pub. Date: Mar. 8, 2018

(65) Prior Publication Data
US 2019/0240471 A1    Aug. 8, 2019

Related U.S. Application Data

(60) Provisional application No. 62/383,142, filed on Sep. 2, 2016.

(51) Int. Cl.
*A61M 37/00*  (2006.01)
*A61K 49/22*  (2006.01)
(Continued)

(52) U.S. Cl.
CPC ......... *A61M 37/0092* (2013.01); *A61B 5/055* (2013.01); *A61B 8/0833* (2013.01);
(Continued)

(58) Field of Classification Search
CPC ...... A61M 37/0092; A61M 2037/0007; A61B 5/055; A61B 8/0833; A61K 38/00;
(Continued)

(56) References Cited

U.S. PATENT DOCUMENTS 7,687,026 B2    3/2010 Laugharn, Jr.
2003/0147812 A1*  8/2003 Ueberle ................. A61B 8/481
424/9.52
(Continued)

OTHER PUBLICATIONS

Cao et al., Configurations and control of magnetic fields for manipulating magnetic particles in microfluidic applications: magnet systems and manipulation mechanisms, Lab Chip 2014, 14, 2762-2777, Royal Society of Chemistry, DOI:10.1039/C4LC00367E (Year: 2014).*

(Continued)

*Primary Examiner* — John Denny Li
(74) *Attorney, Agent, or Firm* — QUARLES & BRADY LLP

(57) ABSTRACT

The present disclosure includes system, methods, and kits relating to creating a second structure with a plurality of first structures at a target site inside or adjacent to a host object. The methods include the step of generating a field that non-invasively penetrates into the host object. The methods further include the step of positioning a first portion of the plurality of first structures at the target site using a force corresponding to the field. Additionally, the methods include the step of linking the first portion of the plurality of first structures with one another and/or the host object at the target site to form the second structure.

15 Claims, 15 Drawing Sheets

(51) Int. Cl.
  *A61K 41/00* (2020.01)
  *A61B 8/08* (2006.01)
  *A61B 5/055* (2006.01)
  *A61N 2/00* (2006.01)
  *A61K 38/00* (2006.01)

(52) U.S. Cl.
  CPC ........ *A61K 41/0028* (2013.01); *A61K 49/223* (2013.01); *A61N 2/004* (2013.01)

(58) Field of Classification Search
  CPC .. A61K 41/0028; A61K 49/223; A61N 2/004; A61N 2/002
  See application file for complete search history.

(56) References Cited

U.S. PATENT DOCUMENTS

| | | | |
|---|---|---|---|
| 2006/0025713 A1* | 2/2006 | Rosengart | A61K 9/0009 604/5.02 |
| 2010/0160897 A1 | 6/2010 | Ducharme | |
| 2011/0118820 A1 | 5/2011 | Sandhu | |
| 2011/0142937 A1* | 6/2011 | Macdonald | A61K 9/5078 424/484 |
| 2012/0141552 A1 | 6/2012 | Dalecki | |
| 2012/0158047 A1 | 6/2012 | Edwards | |
| 2013/0330389 A1 | 12/2013 | Fabiilli | |
| 2014/0271897 A1* | 9/2014 | Pathak | A61K 31/7036 424/497 |
| 2015/0118692 A1* | 4/2015 | Johnson | G01N 33/54313 435/7.5 |
| 2015/0165091 A1 | 6/2015 | Dalecki | |
| 2016/0060655 A1* | 3/2016 | Quake | C12N 15/86 424/94.61 |
| 2016/0243377 A1* | 8/2016 | Weinberg | A61N 2/02 |

OTHER PUBLICATIONS

Dayton PA, et al. The magnitude of radiation force on ultrasound contrast agents. The Journal of the Acoustical Society of America 112, 2183-92 (2002).

Feshitan JA, et al. Microbubble size isolation by differential centrifugation. Journal of colloid and interface science 329, 316-24 (2009).

International Searching Authority, International Search Report and Written Opinion for PCT/US2017/049850, dated Jan. 9, 2018, 11 pages.

Kelly JF, et al. Injury Severity and Causes of Death From Operation Iraqi Freedom and Operation Enduring Freedom: 2003-2004 Versus 2006. The Journal of Trauma 64, S21-S27 (2008).

Keriquel, V., et al. "In vivo bioprinting for computer-and robotic-assisted medical intervention: preliminary study in mice." Biofabrication 2.1 (2010): 014101.

Martin M, et al. An Analysis of In-Hospital Deaths at a Modern Combat Support Hospital. The Journal of Trauma 66, S51-S61 (2009).

Tiukinhoy-Laing SD, et al. Ultrasound-facilitated thrombolysis using tissue-plasminogen activator-loaded echogenic liposomes. Thrombosis research 119, 777-84 (2007).

\* cited by examiner

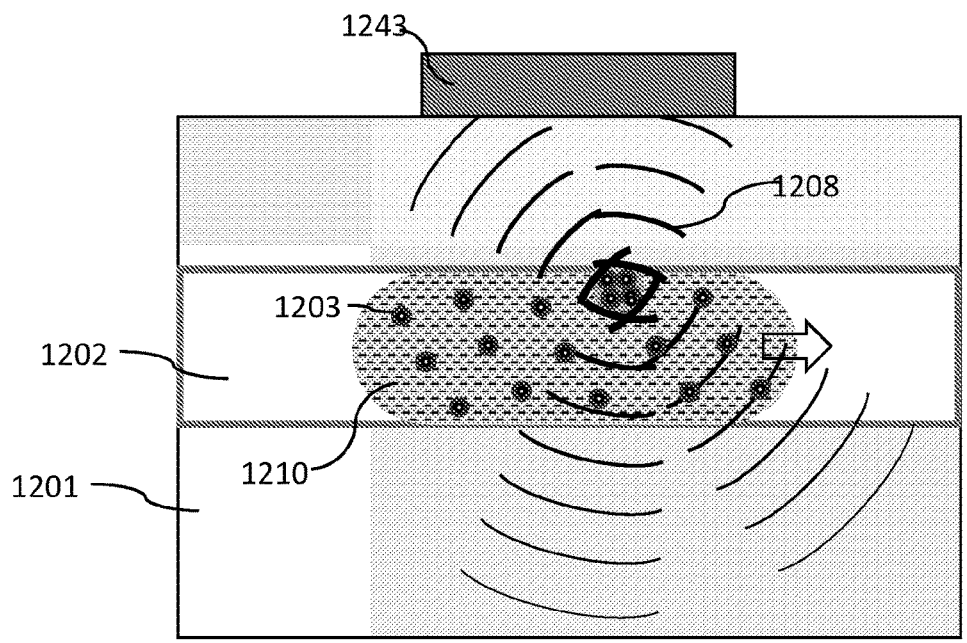
FIG. 12A
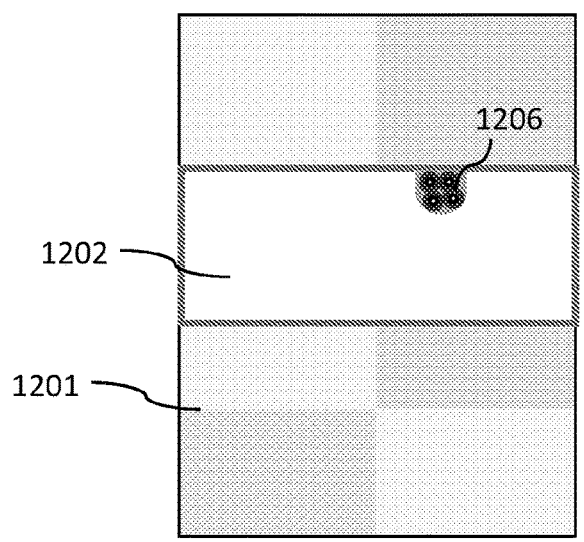 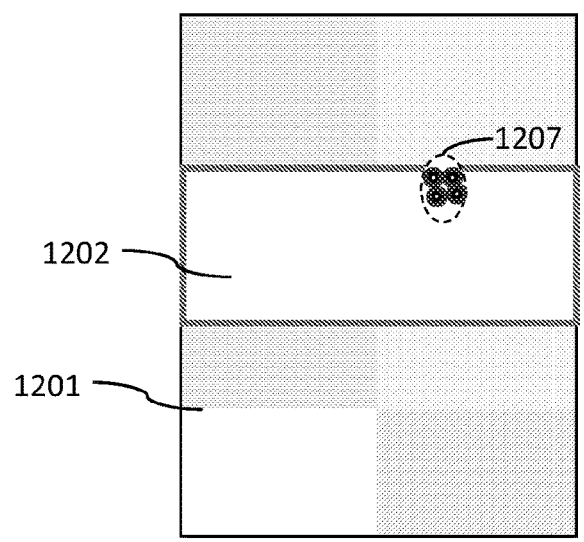
FIG. 12B        FIG. 12C

METHODS AND SYSTEMS FOR NON-CONTACT CONSTRUCTION OF AN INTERNAL STRUCTURE

CROSS-REFERENCE TO RELATED APPLICATIONS

This application represents the national stage entry of PCT/US2017/049850 filed Sep. 1, 2017, which claims benefit of U.S. Provisional Patent Application 62/383,142, filed Sep. 2, 2016. The contents of these applications are hereby incorporated by reference as set forth in their entirety herein.

BACKGROUND OF THE INVENTION

Various aspects of the present disclosure relate generally to methods and systems, which construct a structure inside a host object in a non-contact manner.

The current paradigm of manufacturing a structure inside a host object, whether done in an additive or subtractive manner, requires direct access to the site. In medical practice, interventions on an internal tissue (e.g. to stop bleeding from an intra-abdominal organ, place an intra-cavity implant, embolize a blood vessel, break up a thrombus or remove a piece of diseased tissue), require either open surgery or another invasive technique such as catheterization or endoscopic operation. These current methods usually involve complicated procedures, which often cannot be carried out in a timely manner due to a limitation in resources and/or a lack of sterile environment in ambulatory settings (e.g. in combat zones). In addition, current intervention techniques are highly invasive, and often associated with serious adverse effects, such as bleeding, infection, and anesthesia complications.

Therefore, what is needed is a simplified method to create an internal structure inside a host subject in a non-destructive manner.

SUMMARY OF THE INVENTION

The foregoing needs are met by the methods, systems, and/or kits for non-destructive construction of a structure inside a host object according to the disclosure.

Various aspects of the present disclosure may generally relate to methods and systems, which perform noninvasive interventions in living subjects. In particular, aspects of the present disclosure relate to methods and systems, which may construct an intra-cavity implant remotely using containing agents that may be associated with substances. The substances may be used to activate a formation of structures. According to some aspects, a field generator may be configured to position the structures at or near the site within the host object.

In one aspect, the present disclosure provides a method for creating a second structure with a plurality of first structures at a target site inside or adjacent to a host object. The method includes the step of generating a field that non-invasively penetrates into the host object. The method further includes the step of positioning a first portion of the plurality of first structures at the target site using a force corresponding to the field. Additionally, the method includes the step of linking the first portion of the plurality of first structures with one another and/or the host object at the target site to form the second structure.

In another aspect, the present disclosure provides a system for creating a second structure from a plurality of first structures at a target site inside or adjacent to a host object, the system including an infusion device configured to introduce the plurality of first structures into or adjacent to the host object. The system further including a field generator configured to generate a field that propagates into the host object and exerts a force on at least one of the plurality of first structures. Additionally, the system including a field generator controller configured to direct the field generator to generate the field following a specific pattern that positions at least one of the plurality of first structures at the target site to form the second structure inside or adjacent to the host object.

In another aspect, the present disclosure provides a system for creating a second structure from a plurality of magnetomotive first structures at a target site inside or adjacent to a host object. The system includes an infusion device configured to introduce the plurality of magnetomotive first structures into or adjacent to the host object. The system further includes a magnetic field generator configured to generate a magnetic field that propagates into the host object and exerts a force on at least one of the plurality of magnetomotive first structures. Additionally, the system includes a field generator controller configured to direct the magnetic field generator to generate the magnetic field following a specific pattern that positions at least one of the plurality of magnetomotive first structures at the target site to form the second structure inside or adjacent to the host object.

In another aspect, the present disclosure provides a system for creating an intra-cavity implant from a plurality of first structures at a target site inside or adjacent to a host object, the system includes an infusion device configured to introduce the plurality of first structures into a cavity, the cavity including the target site. The system further includes a field generator configured to generate a field that propagates into the host object and exerts a force on at least one of the plurality of first structures. Additionally, the system includes a field generator controller configured to direct the field generator to generate the field that positions at least one of the plurality of first structures at the target site to form a second structure inside or adjacent to the host object. Further, the second structure includes the intra-cavity implant.

In another aspect, the present disclosure provides a system for creating a second structure from a plurality of first structures at a target site inside or adjacent to a host object. The system includes an infusion device configured to introduce the plurality of first structures into or adjacent to the host object, the plurality of first structures comprising gas-filled bubbles containing a substance. The system further includes at least one acoustic transducer configured to generate an acoustic wave that propagates inside or adjacent to the host object and exerts acoustic radiation forces on the bubbles. Additionally, the system includes a controller that directs the at least one acoustic transducer to generate the acoustic wave following a specific pattern, and positions at least one of the bubbles containing the substance at the target site to form the second structure inside or adjacent to the host object.

In another aspect, the present disclosure provides a system for creating a structure from a plurality of containing agents enclosing a substance at a target site inside or adjacent to a host object. The system includes an infusion or injection device configured to introduce the plurality of containing agents into or adjacent to the host object. The system further includes a controller configured to position the plurality of containing agents at a location in the host object. Additionally, the system includes at least one acoustic transducer configured to generate an acoustic wave that propagates inside or adjacent to the host object and exerts an acoustic force on the plurality of containing agents. The acoustic force causes the substance to be released such that a change in the host object occurs to form a first structure within or adjacent to the host object and a continued generation of first structures to create a second structure within or adjacent to the host object.

In another aspect, the present disclosure provides a kit. The kit includes a plurality of first structures. The kit further includes a non-transient computer readable medium containing program instructions for causing a computer that is coupled to an imaging system and an infusion device to perform a method. The method includes imaging a target site within or adjacent to the host object via an imaging element. The method further includes analyzing images of the target site. Further, determining, via the images, a design for a second structure configured to slow blood flow. Additionally, the method includes infusing the plurality of first structures into the host object. The method includes generating a field to guide the first structures to the target site, via a field generator. Additionally, the method includes implementing the design for the second structure.

In another aspect, the present disclosure provides a field-deployable kit. The kit includes an infusion device containing a plurality of first structures, and configured for insertion near a target site within or adjacent to a host object. The kit further includes instructions for using the infusion device. Additionally, the kit includes a field generator including a power supply. The kit includes a non-transient computer readable medium containing program instructions for causing a computer to perform a method including, generating, using the field generator, a field configured to drive the plurality of first structures from an injection site to the target site. The plurality of first structures are configured to link to one another and/or the host object to form a second structure at the target site.

The foregoing and other aspects of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present disclosure will hereafter be described with reference to the accompanying drawings, wherein like reference numerals denote like elements.

FIG. 12A is a diagram illustrating an aspect of the present disclosure, which performs an intervention using acoustic radiation force in a hollow organ.

FIG. 12B is a diagram further illustrating the aspect of FIG. 12A in accordance with the present disclosure, FIG. 12C is a diagram further illustrating the aspect of FIG. 12A in accordance with the present disclosure.

DETAILED DESCRIPTION

Figure 1:
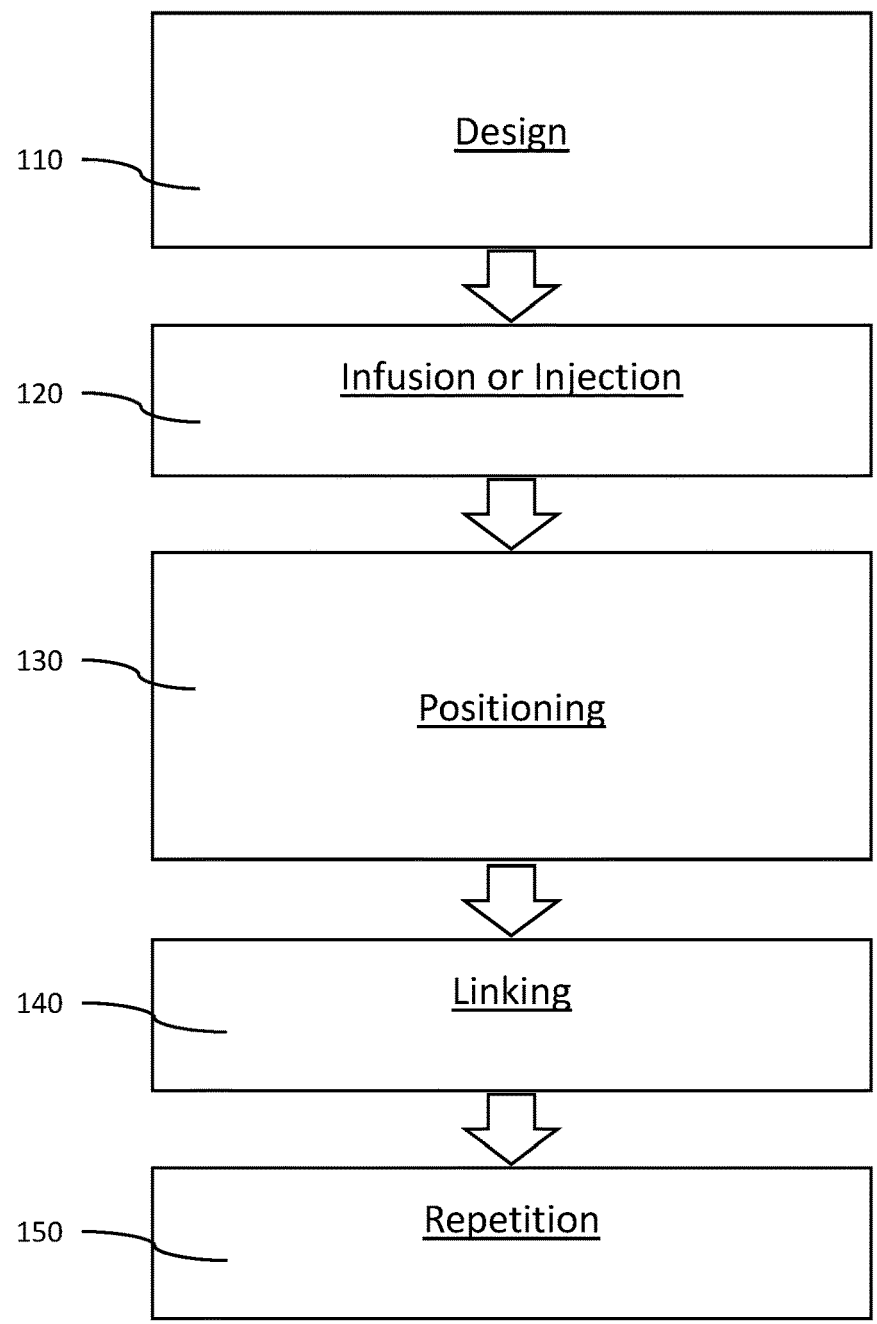
FIG. 1 is a flow diagram illustrating a process for contactless construction of an internal structure according to the present disclosure.

Before the present invention is described in further detail, it is to be understood that the invention is not limited to the particular aspects described. It is also to be understood that the terminology used herein is for the purpose of describing particular aspects only, and is not intended to be limiting. The scope of the present invention will be limited only by the claims. As used herein, the singular forms "a", "an", and "the" include plural aspects unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Aspects referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive of their endpoints. For example, a numeric range of between 1 and 10 includes the values 1 and 10. When a series of numeric ranges are disclosed for a given value, the present disclosure expressly contemplates ranges including all combinations of the upper and lower bounds of those ranges. For example, a numeric range of between 1 and 10 or between 2 and 9 is intended to include the numeric ranges of between 1 and 9 and between 2 and 10. As used herein, a "portion" of a "plurality" can include one or more of the plurality.

In an aspect, the present disclosure provides a method for creating a second structure with a plurality of first structures at a target site inside a host object. The method includes: a) generating a field that non-invasively penetrates into the host object, b) positioning at least one of the plurality of first structures at the target site using a force corresponding to the field, and c) linking the at least one of the plurality of first structures with the host object at the target site to form the second structure, wherein the second structure is different from the at least one of the plurality of first structures.

In an aspect, the present disclosure provides a method for creating a second structure with a plurality of first structures at a target site inside or adjacent to a host object. The method includes: a) generating a field that non-invasively penetrates into or through the host object, b) positioning a first portion of the plurality of first structures at the target site using a force corresponding to the field, and c) linking the first portion of the plurality of first structures with one another and/or the host object at the target site to form the second structure.

The linking of step c) may be caused by at least one of a chemical bond, a magnetic force, heat, and an electrostatic force. The method may further include: d) linking a second portion of the plurality of first structures to the first portion of the plurality of first structures. Additionally, the linking of step d) may be caused by at least one of a chemical bond, a magnetic force, heat, and an electrostatic force.

The method may further include imaging the target site to determine a desired position of the first portion of the plurality of first structures, prior to step a). Additionally, the linking of step c) may inhibit a blood flow via the second structure.

Alternatively, the method may further include: d) stopping the generated field once the second structure is formed, e) applying a second force to the second structure, and f) positioning the second structure at a second target site.

In an aspect, the method may further include: d) driving the second structure to a second target site via the field. Additionally, the method may include e) positioning the second structure at the second target site, wherein the second target site is different than the target site.

In an aspect, the field may be an acoustic field. Further, the acoustic field may include a standing wave and the target site may be located at one of a standing wave node or a standing wave antinode. Alternatively, the field may be a magnetic field or an electric field.

In another aspect, the present disclosure provides a system for creating a second structure from a plurality of first structures at a target site inside or adjacent to a host object. The system includes: an infusion device configured to introduce the plurality of first structures into or adjacent to the host object, a field generator configured to generate a field that propagates into the host object and exerts a force on at least one of the plurality of first structures, and a field generator controller configured to direct the field generator to generate the field following a specific pattern that positions at least one of the plurality of first structures at the target site to form the second structure inside or adjacent to the host object. Additionally, the field generator may be at least one of an acoustic transducer, photoacoustic transducer, an electric field generator, and a magnetic field generator.

In another aspect, the present disclosure provides a system for creating a second structure from a plurality of magnetomotive first structures at a target site inside or adjacent to a host object, the system including: an infusion device configured to introduce the plurality of magnetomotive first structures into or adjacent to the host object, a magnetic field generator configured to generate a magnetic field that propagates into the host object and exerts a force on at least one of the plurality of magnetomotive first structures, and a field generator controller configured to direct the magnetic field generator to generate the magnetic field following a specific pattern that positions at least one of the plurality of magnetomotive first structures at the target site to form the second structure inside or adjacent to the host object.

In another aspect, the present disclosure provides a system for creating an intra-cavity implant from a plurality of first structures at a target site inside or adjacent to a host object, the system including: an infusion device configured to introduce the plurality of first structures into a cavity, the cavity including the target site, a field generator configured to generate a field that propagates into the host object and exerts a force on at least one of the plurality of first structures, and a field generator controller configured to direct the field generator to generate the field that positions at least one of the plurality of first structures at the target site to form a second structure inside or adjacent to the host object. The second structure includes the intra-cavity implant. Additionally, the field generator may be at least one of an acoustic transducer, photoacoustic transducer, an electric field generator, and a magnetic field generator.

In another aspect, the present disclosure provides a system for creating a second structure from a plurality of first structures at a target site inside or adjacent to a host object, the system including: an infusion device configured to introduce the plurality of first structures into or adjacent to the host object, the plurality of first structures comprising gas-filled bubbles containing a substance, at least one acoustic transducer configured to generate an acoustic wave that propagates inside or adjacent to the host object and exerts acoustic radiation forces on the bubbles, and a controller that directs the at least one acoustic transducer to generate the acoustic wave following a specific pattern, and positions at least one of the bubbles containing the substance at the target site to form the second structure inside or adjacent to the host object.

Additionally, the at least one of the bubbles may attract at least one native blood component. And, the at least one native blood component may include at least one of platelets, fibrinogen, thrombin, red blood cells, and while blood cells.

In another aspect, the present disclosure provides a system for creating a structure from a plurality of containing agents enclosing a substance at a target site inside or adjacent to a host object, the system including: an infusion or injection device configured to introduce the plurality of containing agents into or adjacent to the host object, a controller configured to position the plurality of containing agents at a location in the host object, and at least one acoustic transducer configured to generate an acoustic wave that propagates inside or adjacent to the host object and exerts a force (such as a cavitation force, or an acoustic radiation force) on the plurality of containing agents, wherein the force causes the substance to be released such that a change in the host object occurs to form a first structure within or adjacent to the host object and a continued generation of first structures to create a second structure within or adjacent to the host object.

Additionally, the release of the substance may cause a reaction of polymerization, chemical cross-linking, or activation of a cascade in the host object.

In reference to the above aspects, the present disclosure further includes wherein the infusion or injection device may be a syringe, a material injector, an infusion pump, or an intravenous catheter. Additionally, the at least one acoustic transducer may be a photoacoustic transducer.

In reference to the above aspects, the present disclosure further includes wherein the substance may be a chemical that induces clotting, platelet activation, clotting factor activation, or fibrin formation in a blood vessel. Further, the substance may be a hemostatic or clotting agent. Additionally, the system may further comprising an imaging element configured to image inside or adjacent to the host object.

In another aspect, the present disclosure provides a kit including: a plurality of first structures, and a non-transient computer readable medium containing program instructions for causing a computer that is coupled to an imaging system and an infusion device to perform a method comprising the steps of: a) imaging a target site within or adjacent to the host object via an imaging element, b) analyzing images of the target site, c) determining, via the images, a design for a second structure configured to slow blood flow, d) infusing the plurality of first structures into the host object, e) generating a field to guide the first structures to the target site, via a field generator, and f) implementing the design for the second structure.

In some aspects, the kit further includes: g) imaging the target site during the implementing of step f), and h) adjusting the design during the implementing of step f) according to at least one image acquired after the implementing of step f) has begun.

In another aspect, the present disclosure provides a field-deployable kit including: an infusion device containing a plurality of first structures, and configured for insertion near a target site within or adjacent to a host object, instructions for using the infusion device, a field generator including a power supply, and a non-transient computer readable medium containing program instructions for causing a computer to perform a method of: a) generating, using the field generator, a field configured to drive the plurality of first structures from an injection site to the target site, and wherein the plurality of first structures are configured to link to one another and/or the host object to form a second structure at the target site.

With reference to the above aspects, the present disclosure further includes wherein the host object may be an object within a human body. Additionally, the plurality of first structures may comprise hemostatic bubbles, thermolytic bubbles, acoustomotive bubbles, or a combination thereof. Further, the second structure may apply a mechanical force on a vessel wall to maintain patency of a lumen.

With reference to the above aspects, the second structure may have a different size and/or shape from the plurality of first structures. Additionally, the plurality of first structures may have an electrostatic charge. Further, the second structure may block blood flow.

With reference to the above aspects, the target site may be an internal bleeding site. Additionally, the second structure may create at least one blood clot. Further, the at least one blood clot may be configured for at least one of controlling bleeding, managing cancer, and treating a vascular malformation. Additionally, the second structure may be configured to lyse a blood clot. In some aspects, the second structure may include an intra-cavity implant.

These aspects are explained in greater detail in the description that follows. Aspects of the disclosure that are described with respect to a method are applicable to aspects related to systems, kits, and other methods of the disclosure, unless the context clearly dictates otherwise. Similarly, aspects of the disclosure that are described with respect to a system are applicable to aspects related to methods, kits, and other systems of the disclosure, and aspects described with respect to a kit are applicable to methods, systems, and other kits of the disclosure, unless the context clearly dictates otherwise.

FIG. 1 illustrates a process of constructing an internal structure inside an object (e.g. a human body or an anatomical structure therein) using a force provided by a non-destructive field according to the present disclosure. In some aspects, the field may be an acoustic, electromagnetic, magnetic or electric field. In some aspects, the force may accordingly be an acoustic radiation force, acoustic streaming force, optical radiation force, magnetic force or electrostatic force. Beginning at process block 110, a region of interest (e.g. a site) inside an object may be identified and/or visualized with an imaging apparatus. An internal structure to be built therein may then be designed. If the desired size of the internal structure is substantially large, the planned construction may be further decomposed into a plurality of smaller structures, which may be built separately in time and/or space.

The imaging apparatus may also evaluate any relevant properties of the host object near the targeted site, which may be used in planning the fabrication process. While the construction may be done with intrinsic material (e.g. cells, platelets, fibrinogen, fibrin, and/or intrinsic and/or extrinsic clotting factors), it may also be done with exogenous first structures (e.g. unit structures), which may be introduced into the host object at process block 120. In some aspects, the first structures may be introduced into the host object via injection or infusion. Each first structure may contain at least one element that may be navigated or driven by the force provided by the field.

At process block 130, an external apparatus (e.g. a field generator) may generate at least one non-destructive field inside the host object near a first construction site. The field may be designed to have a pattern, and may exert a force on at least one first structure to localize it at or steer it to the first site.

At process block 140, the first structures located near the first construction site may interact with each other or the host and form a stable part of the internal, second structure there. In some aspects, the interaction between the first structures and/or the host may use at least one of a chemical bond, thermal process, acoustic force, magnetic force, and electrostatic force. In certain situations, the first structures may interact with each other or the host and form a part of the second structure, which may be subsequently directed by a force generated by a non-destructive field (e.g. by the field generator or a second field generator), a local flow, or its own gravity or buoyancy to fully form the second structure at a second site.

The affixation may also be initiated or facilitated by an acoustic wave, electromagnetic wave, magnetic wave, or heat provided by an external apparatus (e.g. the field generator or the second field generator). The affixation alternatively may be accomplished using intrinsic affixation molecules that may reside in the host. The intrinsic affixation molecules may be activated via the field acting on the at least one first structure, or on other molecules, compounds, or structures associated with the host object. In certain situations, it may be advantageous that the field-motive parts in the first structures are released during or after affixation. This may help to stabilize the second structure amid any subsequent construction.

In certain situations, multiple, smaller structures corresponding to the second structure may built simultaneously at multiple first sites.

At process block 150, process blocks 130 and 140 may be repeated to construct any remaining parts of the second structure until the final internal, second structure is completed. The construction process may be monitored in real-time with the imaging apparatus and be adjusted accordingly if necessary.

The imaging, structure design, construction planning and implementation, and/or field design and generation may be assisted by an automated computer program. The imaging and/or sequential construction at multiple sites may be done in a robotic manner (e.g. via automated equipment, automated medical devices).

Figure 2A:
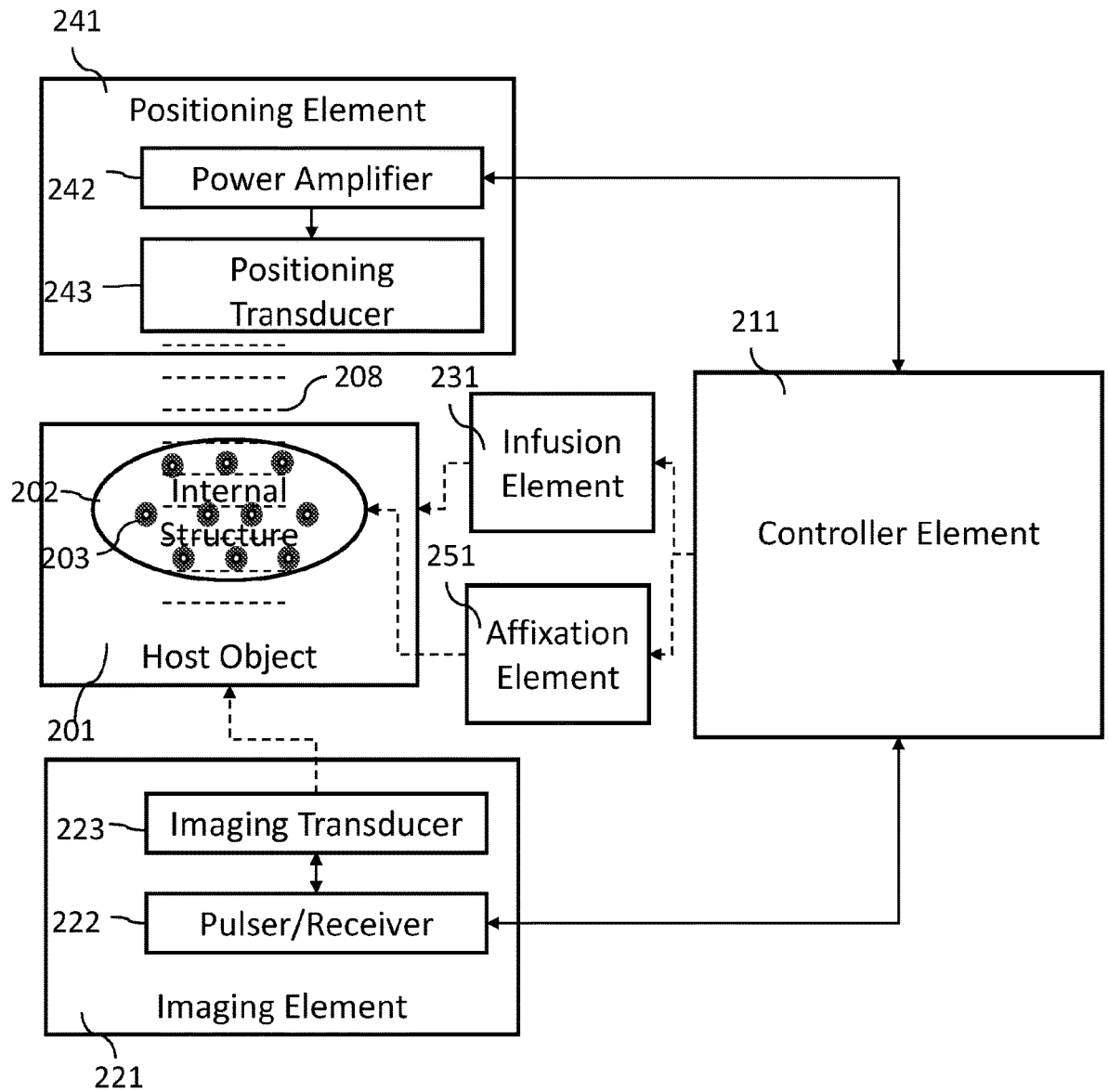
FIG. 2A is a block diagram illustrating a system for non-contact construction of an internal structure using an acoustic field according to the present disclosure.
Figure 2B:
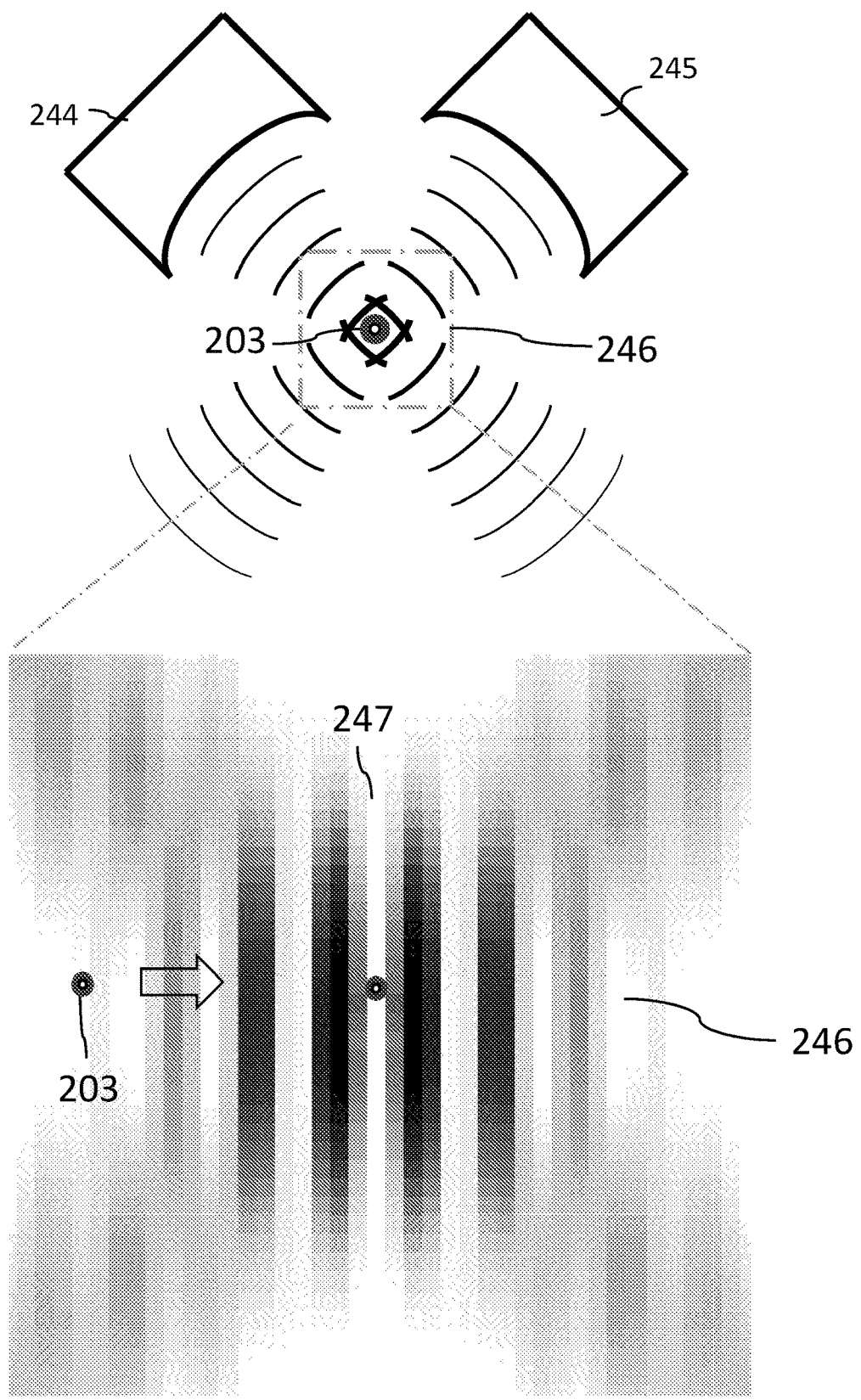
FIG. 2B illustrates a system according to the present disclosure, which generates an acoustic standing-wave field for trapping first structures at a site.

FIGS. 2A and 2B illustrate a system, in accordance with the present disclosure, for non-contact construction of a second structure 202 inside a host object 201 (e.g. a human body or internal anatomical structure) using an acoustic field 208. In some situations, it may be beneficial to use a field generator to generate an acoustic field 208. The system may include a controller 211 (e.g. a computer), an imaging element 221, an infusion (or injection) element 231, a positioning element 241 and, in some aspects, an affixation element 251.

The imaging element 221 may visualize the inside of the host object 201 and may obtain relevant geometrical and/or environmental information (e.g. flow, temperature, molecular composition and/or chemical environment) from the targeted site. The imaging element 221 may capture/record images and/or provide real-time viewing of the site. In some aspects, the imaging element 221 may be an ultrasonography, photoacoustic imaging, thermoacoustic imaging, magnetoacoustic imaging, X-ray computed tomography, magnetic resonance imaging, nuclear or optical imaging apparatus, or any other known medical imaging device.

For example, an imaging element 221 performing ultrasonography may further comprise a pulser/receiver 222 to drive an imaging acoustic transducer 223 (e.g. a piezoelectric transducer array). The imaging acoustic transducer 223 may emit a sound wave and acquire the reflected sound wave from the host object 201 to form at least one image of the inside of the host object 201. The at least one image may then be used for the design of the second structure 202.

In some aspects, the infusion element 231 (e.g. a syringe, a material injector, an infusion pump, or an intravenous catheter) may be utilized to perfuse the host object 201 with first structures or compounds 203, which may contain at least one acoustomotive part. The acoustomotive part may have at least one acoustic property (e.g. density, speed of sound, acoustic impedance, acoustic absorption, sound reflectivity, sound attenuation) that is substantially different from that of the host object 201 near the construction site. In certain situations, such as if used in living host objects, it may be advantageous to have the first structures or compounds made of biocompatible and/or biodegradable material. As one non-limiting example, the acoustomotive first structures 203 may be in the form of bubbles, which may contain at least one gas-filled core stabilized by a shell made of lipid, protein and/or polymer. Additional building materials may be loaded onto or into the shell, through for example ligand binding, electrostatic attraction or hydrophobic interaction.

In the positioning element 241, a power amplifier 242 may drive a positioning acoustic source 243 (e.g. at least one piezoelectric transducer or at least one microphone) to generate an acoustic field 208 (e.g. an acoustic field) inside the host object 201. The acoustic field 208 may apply an acoustic radiation force or an acoustic streaming force on the first structures 203, and may trap them at or direct them to a targeted site.

To trap the first structures 203, the acoustic field 208 may feature a standing wave, which may contain at least one stationary low-pressure region (node) or at least one stationary high-pressure region (antinode). When a field pressure gradient is sufficient, the force provided by the acoustic field 208 may overcome a drag force originated by an ambient flow, a gravity force or a buoyant force. As a result, when the first structures 203 travel through the acoustic field 208, the first structures 203 may be trapped at either a node or an antinode. The use of a node or an antinode may depend on the frequency of the acoustic field 208 or the size and acoustic impedance of acoustomotive structures.

The acoustic field 208 may be capable of localizing the first structures 203 in 1D, 2D and 3D, and may take different patterns (e.g. plane, cylinder, sphere, Bessel, gratings, bottle, donut, grid, net, trap, or the like), and may be generated by adjusting the number, geometry, location, output energy, frequency and/or phase of the at least one positioning acoustic sources 243. For example, as illustrated in FIG. 2B, two spherically focused acoustic transducers 244 and 245 may emit two acoustic traveling waves of the same energy and frequency but with a phase difference of 180 degrees. When the traveling waves are arranged with overlapped focus, an acoustic standing-wave field 208 as a 1-D trap may be formed at the focal zone with a pressure node 247 in the middle. When a first structure 203 (e.g. a gas-filled bubble) with a resonance frequency lower than the emission frequency of the acoustic transducers 244 and 245 travels through the acoustic field 208, the first structure 203 may be attracted to the pressure node 247. In addition, in order to facilitate the admission of the first structure 203 into the trapping zone, at least part of the acoustic field 208 may be turned off temporally. The off-time may be short, so that the already trapped first structures may not escape from the trap.

To direct the first structures 203 to a target site, the acoustic trap may be moved to navigate the trapped first structures. Alternatively, an acoustic traveling wave may be generated to apply an acoustic radiation force on the first structures 203, adjust their trajectory or drive them to the site.

Next, the first structures 203 may interact with each other and/or the host object 201 at the targeted site, through an attraction force (e.g. an acoustic secondary Bjerknes force, a magnetic force, an electric force), a chemical reaction (e.g. cross-linking, gelation, polymerization) or a biological synthesis process (e.g. cell adhesion and/or remodeling, clot formation). The optional affixation element 251 may be further included to direct to the construction site at least one of acoustic waves, magnetic waves, electromagnetic waves, or heat. Accordingly, the optional affixation element 251 may facilitate the interaction between the first structures 203 and/or between the first structures 203 and the host object 201 to complete construction of at least a part of the second structure 202.

The controller 211 (e.g. a computer) may analyze data from the imaging element 221 to obtain the local information near the construction site of the host object 201, develop a construction plan to build the second structure 202. The controller 211 may perform the above via automated software. Accordingly, in some aspects, the controller 211 may coordinate the infusion element 231, the positioning element 241 and the affixation element 251 to construct the second structure 202. In some aspects, the construction of the second structure 202 may occur in a robotic manner (e.g. using automated devices, automated medical devices). In some aspects, the same acoustic transducer may also be used to perform a plurality of functions, such as imaging, positioning and/or affixation.

Figure 3:
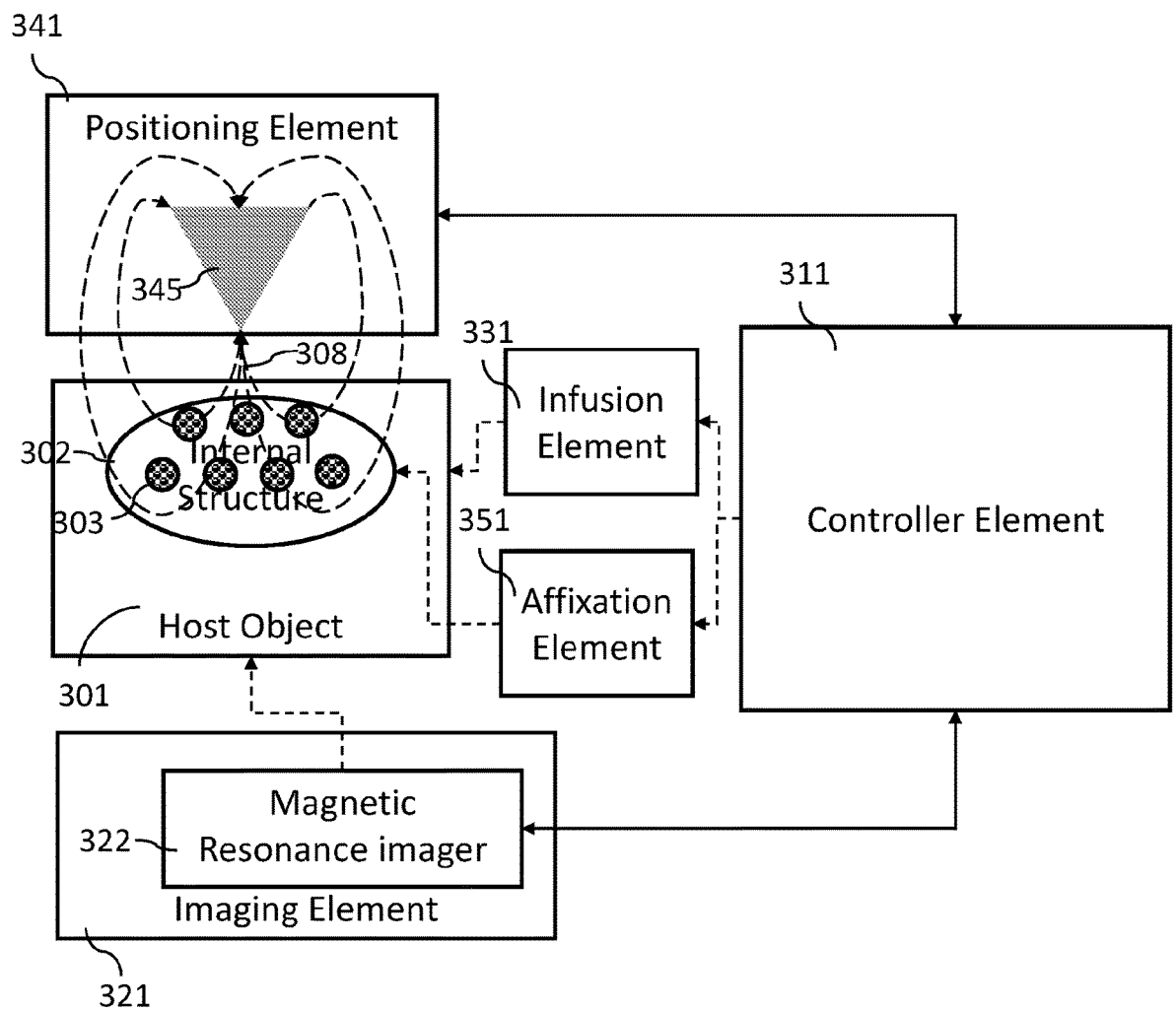
FIG. 3 is a block diagram illustrating a system for non-contact construction of an internal structure using a magnetic field according to the present disclosure.

FIG. 3 is another non-limiting system for non-contact construction of a second structure 302 inside a host object 301, here using a magnetic field 308. In one aspect, magnetomotive first structures 303 contain at least one magnetic particle, which may be made of a ferromagnetic material (e.g. iron, cobalt, nickel, their alloy composite, magnetite), a paramagnetic material (e.g. gadolinium, magnesium, molybdenum, lithium, tantalum), a diamagnetic material (e.g. copper) or a bio-derived magnetic protein.

After introduction into the host object 301 by an infusion element 331, the magnetomotive first structures 303 may be attracted or navigated to a targeted site by a magnetic field 308. The magnetic field 308 may be generated from a magnet 345 in a positioning element 341. In some aspects, the magnet 345 may take the form of a permanent magnet or an electromagnet. Next, the first structures 303 may interact with each other or the host object 301 and form a part of the second structure 302. In some aspects, an affixation element 351 may be included. The affixation element 351 may function similarly to the previously described affixation element 251.

Still referring to FIG. 3, in some aspects the infusion, positioning and affixation may be repeated at other sites until the entire second structure 302 is built. In one aspect, an imaging element 321 (for example in the form of a magnetic resonance imager 322) may produce at least one image of the host object 301 to assist with structure design, construction planning, and/or adjustment. In some aspects, the electromagnets in the magnetic resonance imager 322 (e.g. the gradient coil) may be used for positioning or navigating the first structures 303.

A controller 311 may function similarly to the previously described controller 211.

Figure 4:
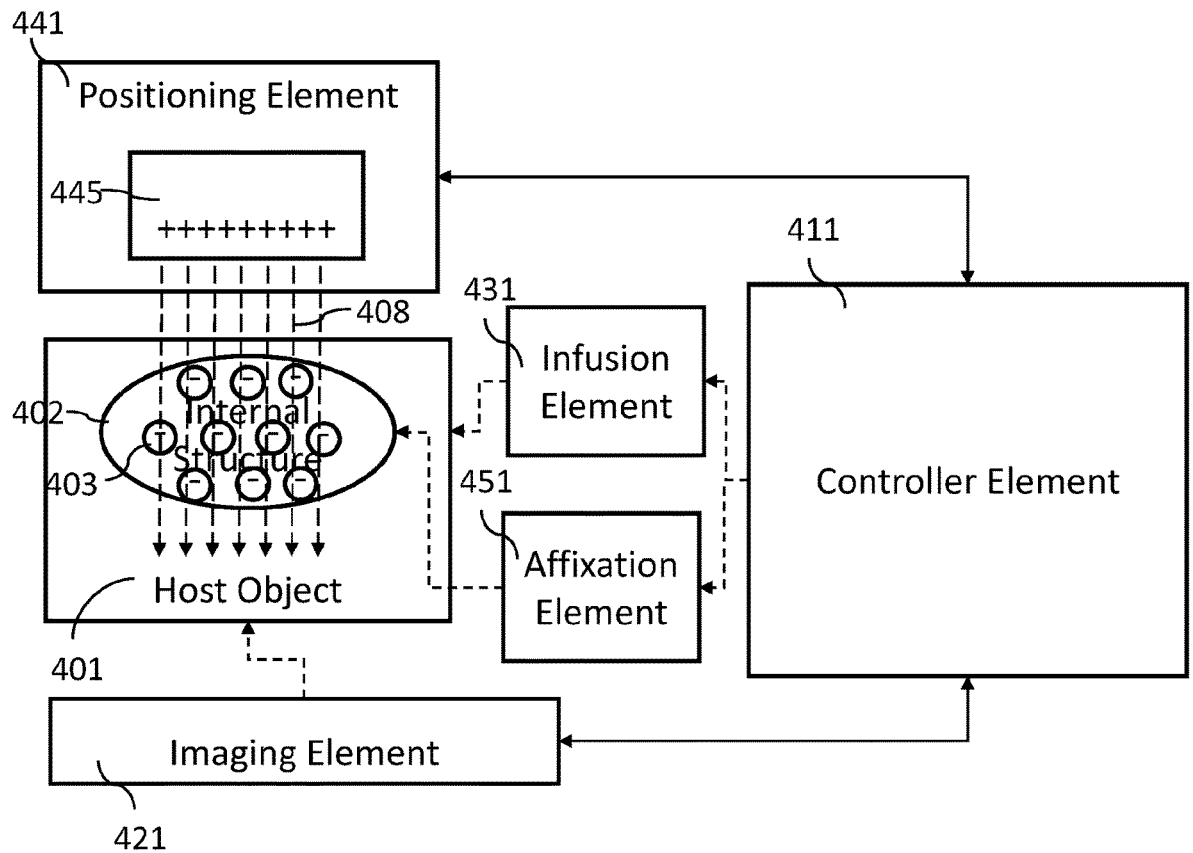
FIG. 4 is a block diagram illustrating a system for non-contact construction of an internal structure using an electric field according to the present disclosure.

FIG. 4 is yet another non-limiting system for non-contact construction of a second structure 402 inside a host object 401, here using an electric field 408. In some aspects, charged first structures 403 may be introduced by an infusion element 431, and positioned at a targeted site by an electric field 408. The electric field 408 may be generated by a generator 445. Similarly to the above description of FIGS. 2 and 3, the first structures 403 may then interact with each other or the host object 401 at the targeted site to form a part of the second structure 402. The infusion, positioning and affixation steps may be repeated at other sites until the desired second structure 402 is completed.

In some aspects, a controller 411 may function similarly to the previously described controller 211. Further, in some aspects, an imaging element 421 may function similarly to the previously described imaging element 221. In some aspects, an affixation element 451 may be included. The affixation element 451 may function similarly to the previously described affixation element 251. Additionally, a positioning element 441 may be included that functions similarly to the previously described positioning element 241.

FIG. 5 shows another non-limiting aspect of the present disclosure working in an additive mode, where a structure is constructed by depositing material, often block by block. For example, rapid termination of internal bleeding is of utmost importance when managing trauma patients. In the current clinical practice, definitive management of internal hemorrhage requires open surgery, which is often impractical to be performed in a sufficiently short time. As another example, therapeutic endovascular embolization is a procedure that blocks blood vessels to control bleeding, limit cancer progress by starving tumor cells, close varicose veins, and correct a vascular malformation (e.g. arteriovenous malformation, aneurysm). While it is a less invasive procedure, endovascular embolization usually done through catheterization is still associated with a significant risk of bleeding, infection, and vascular damage. An aspect of the present disclosure provides a system that may be capable of deliberately creating blood clots within a blood vessel, and in a non-invasive manner. This system may therefore be used to control bleeding, manage cancer, and treat a vascular malformation.

Figure 5A:
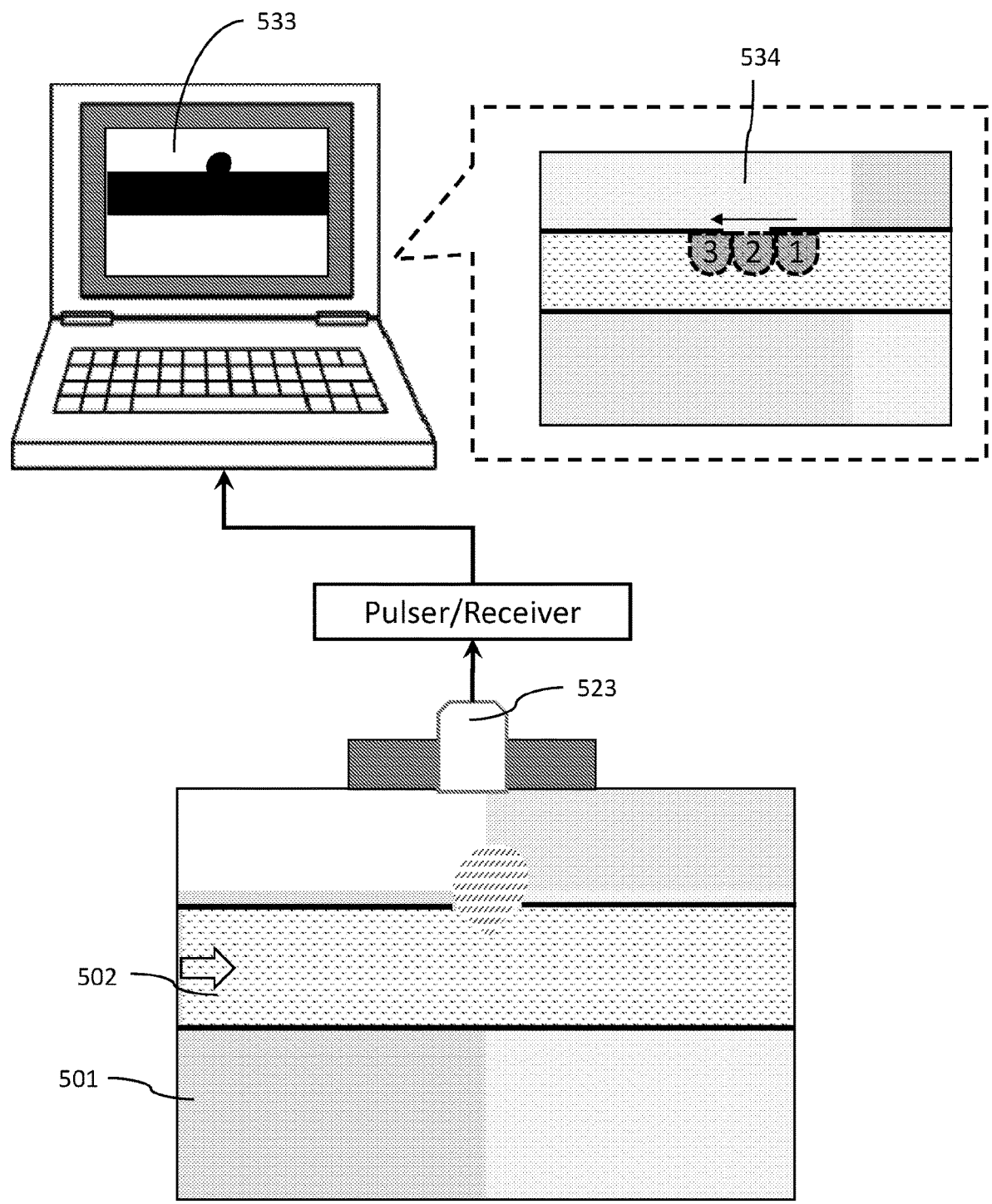
FIG. 5A is a graph illustrating an aspect of the present disclosure working in an additive mode to perform noninvasive therapeutic embolization.

First, as illustrated in FIG. 5A, through a focused assessment of the body 501 with an acoustic imaging probe 523, a desired embolization site (e.g. an active bleeding location) in a blood vessel 502 may be identified from sonographic images 533. In certain situations, it may be advantageous to have images acquired in the Doppler or the contrast-enhanced mode. Then, a construction plan 534 may be developed with the assistance of a computer program to form at least one clot at the site.

Figure 5B:
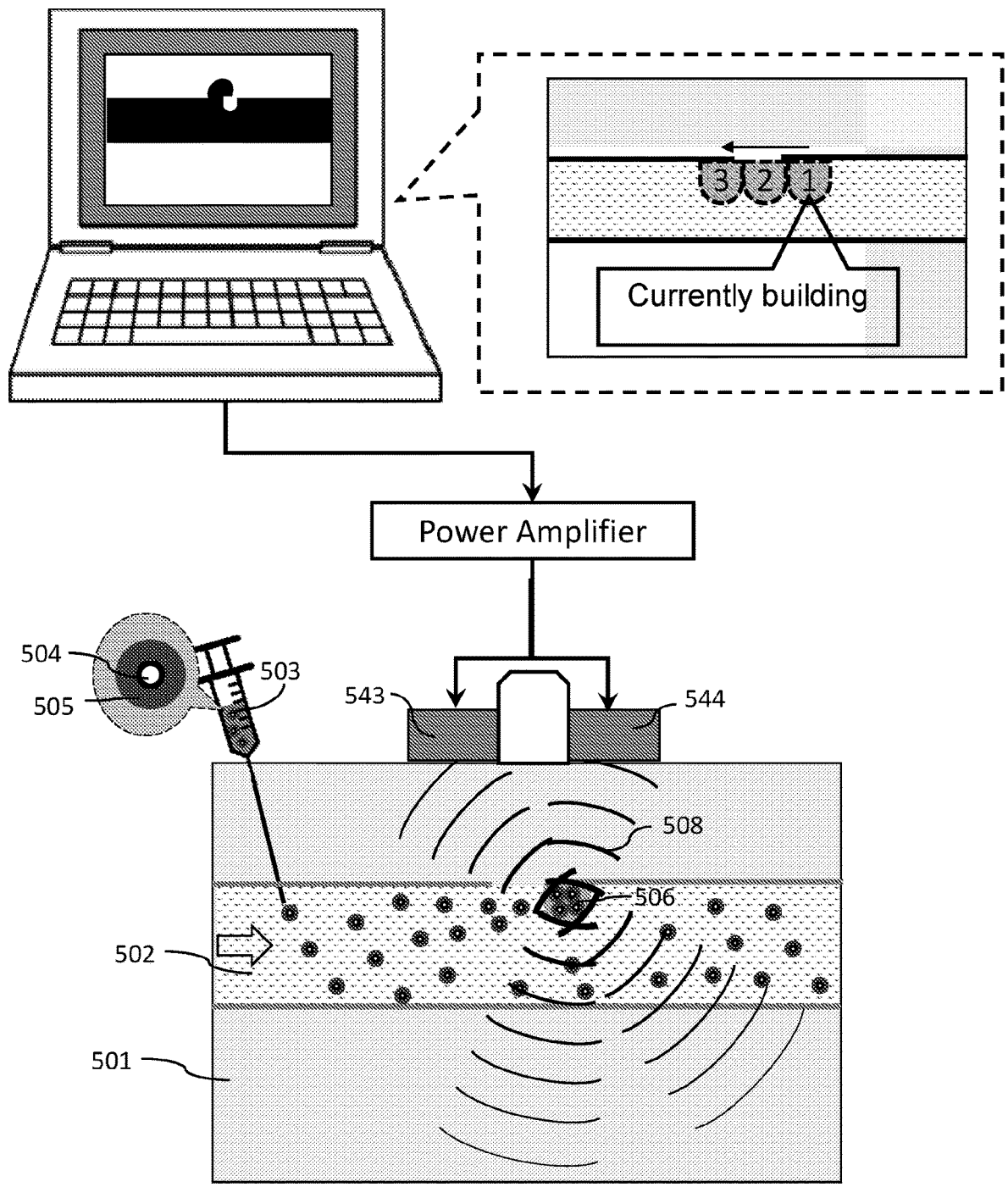
FIG. 5B is a graph illustrating an aspect of the present disclosure working in the additive mode of FIG. 5A.

Next, as illustrated in FIG. 5B, hemostatic agents may be introduced into the body 501 through intravenous injection by a syringe. These hemostatic agents may take the form of acoustomotive bubbles (e.g. hemostatic bubbles 503), which may contain at least one inclusion 504 filled with gas that has low solubility in water or blood—such as air, oxygen, sulfur hexafluoride or perfluorocarbons. The hemostatic bubbles 503 may further contain stabilizing shells 505 made of encapsulating material, such as proteins (e.g. albumin), lipids (e.g. phospholipid) and/or polymers (e.g. PLGA, PVA, chitosan, alginate), etc. Additional hemostatic agents (e.g. platelet, recombinant factor VIIa, prothrombin complex concentrate, tranexamic acid or desmopressin) may also be loaded onto or into the shell 505, through for example ligand binding, electrostatic attraction or hydrophobic interaction. Or, in certain situations it may be advantageous for the hemostatic agents to be encapsulated within the hemostatic bubbles 503 in a manner such that their hemostatic contents are not exposed to blood until released and/or activation at the construction site.

In some aspects, the hemostatic bubbles 503 may be synthesized by, for example, membrane emulsion, mechanical agitation, laser or acoustic cavitation or microfluidic methods. The diameter of the hemostatic bubbles 503 may be smaller than 10 µm, so that they may pass through the capillary network and circulate throughout the body 501 for a time sufficient for clot formation.

To construct a first clot 506, an acoustic field 508 may be introduced to exert acoustic force on the hemostatic bubbles 503 and position at least a fraction of the hemostatic bubbles 503 near the intended construction site. The acoustic field 508 may be generated by an extracorporeal acoustic apparatus. For example, two positioning acoustic transducers 543, 544, flanking the imaging probe 523, may be used to generate two focused sound beams. The focal zone of the two beams may cross at the intended site for the first clot 506, and accordingly generate a localized acoustic standing wave (e.g. acoustic field 508), which may contain a plurality of pressure nodes or antinodes aligned along the blood flow direction at the construction site. When the hemostatic bubbles 503 flow through the acoustic standing wave, they may experience an acoustic radiation force (e.g. the primary Bjerknes force) or an acoustic streaming force that overcomes the blood-flow-induced drag force. Accordingly, the hemostatic bubbles 503 may become trapped in the pressure nodes or antinodes—depending on their size.

In certain situations, it may be advantageous for the sound beams generated by the positioning transducers 543, 544 (e.g. piezoelectric phased array) to have a frequency between 20 KHz~10 MHz. Due to the low attenuation of acoustic wave in soft tissue in this frequency range, the resulting ultrasonic standing wave may trap a plurality of hemostatic bubbles 503 at a multi-centimeter depth in the body 501 without causing damage. The location of the trapped hemostatic bubbles 503 may be further finely adjusted by changing the location of the pressure nodes and antinodes by, for example, modulating the frequency or phase of the sound beams or moving the positioning transducers 543, 544.

Once the hemostatic bubbles 503 are trapped, they may then attract each other as a result of the secondary Bjerknes force and form an immobilized and artificial first clot 506 through a chemical reaction (e.g. gelation, polymerization, chemical cross-linking) between the shell material. Alternatively, the trapped hemostatic bubbles 503 may attract native blood components (e.g. platelets, fibrinogen, thrombin), locally activate the coagulation pathway, and form a first clot 506.

In some aspects, the cross-linked hemostatic bubbles 503 may also provide a scaffold for clot formation. The scaffold may also release the loaded procoagulant factors, which may promote clotting, platelet activation, clotting factor activation, or fibrin formation. As a result, the first clot 506 may be produced by the trapped hemostatic bubbles 503 through activating and/or promoting the native intrinsic and/or extrinsic blood coagulation cascade. In order to prevent destabilizing the first clot 506 during the subsequent construction, gas may be released during clot formation through remodeling of shell material.

According to one aspect, another acoustic wave with high peak negative pressure may also be utilized to break the trapped hemostatic bubbles 503 to help discharge the gas and release the loaded hemostatic agents.

Figure 5C:
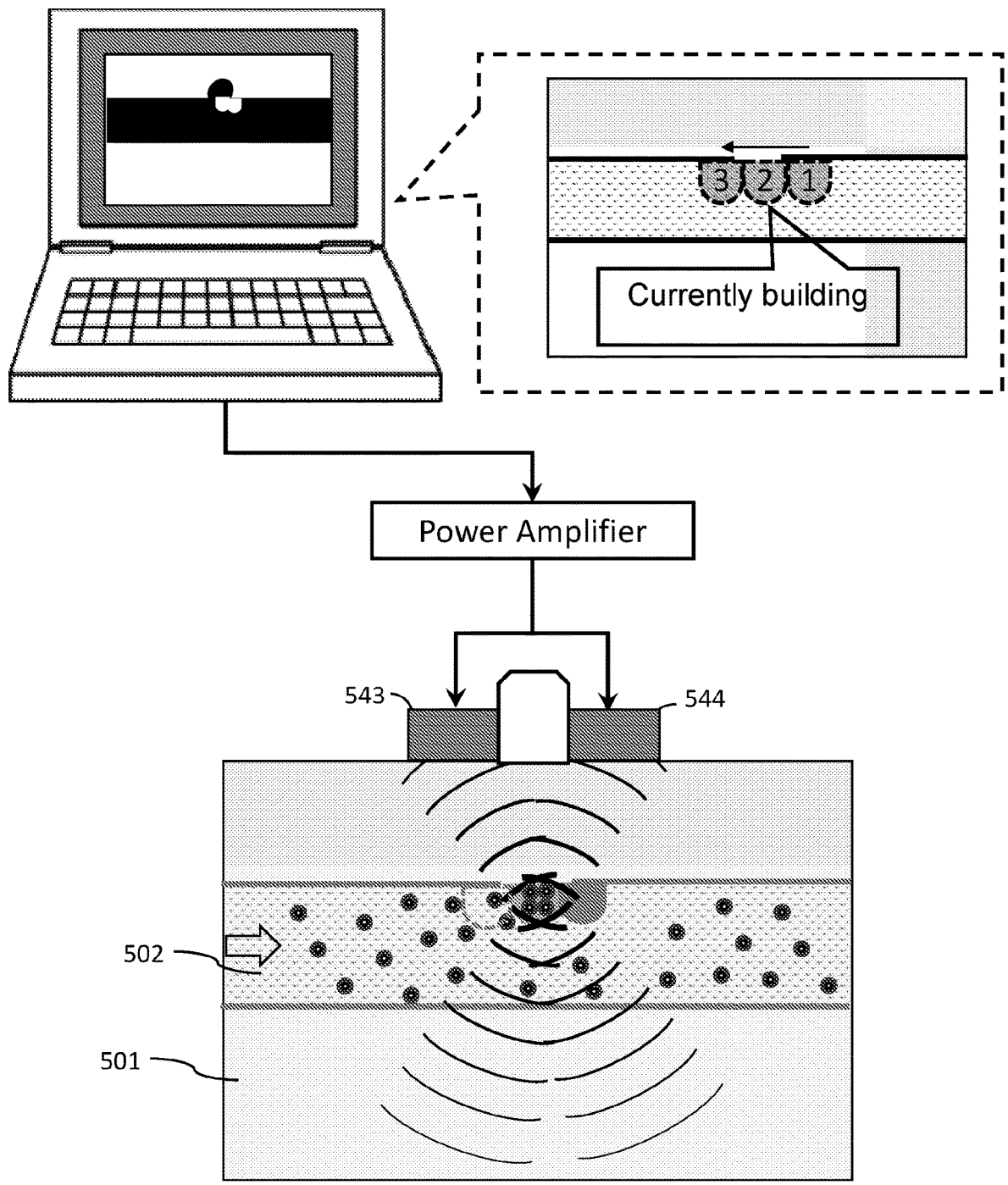
FIG. 5C is a graph illustrating an aspect of the present disclosure working in the additive mode of FIG. 5A.

Finally, as illustrated in FIG. 5C, if necessary, the positioning transducers 543, 544 may generate a standing acoustic wave of different patterns to construct additional clots until the desired embolization is achieved.

Figure 6:
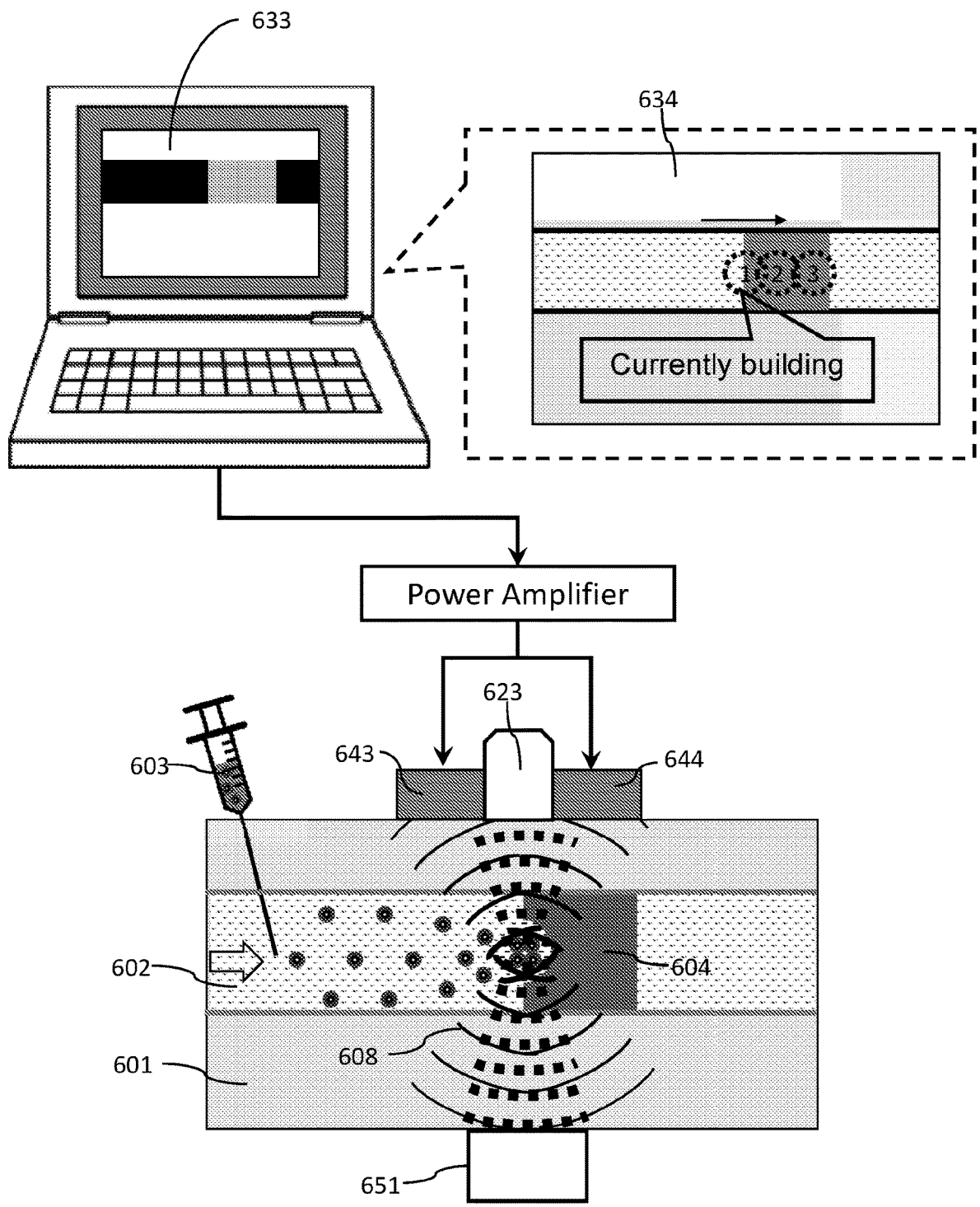
FIG. 6 is a graph illustrating the use of an aspect of the present disclosure working in a subtractive mode to lyse a blood clot.

FIG. 6 illustrates another aspect of the present disclosure, here, working in a subtractive mode, where a structure is constructed by removing material from a stock material. Ischemic heart disease is the leading cause of death in developed countries. In current clinical practice, revascularization in life-threatening myocardial infarction is achieved by either coronary artery bypass grafting (CABG) or percutaneous coronary intervention (PCI). Both CABG and PCI are highly invasive multi-hour operations, which can be done only in well-equipped surgical facilities. They also are associated with serious adverse effects, such as bleeding, infection and arrhythmia.

An aspect of the present disclosure provides a device that may perform angioplasty on a body 601 noninvasively, possibly in ambulatory settings. Here, thrombolytic bubbles 603, which may be loaded with thrombolytic drugs (e.g. tissue plasminogen activator, streptokinase, heparin), are introduced into a clotted blood vessel 602. According to images 633 obtained by an imaging apparatus 623, a plan 634 may be developed to dig a tunnel through a clot 604. Similarly, an acoustic standing wave 608 produced by positioning acoustic transducers 643, 644, may be used to enrich thrombolytic bubbles 603 near a surface of the clot 604 and facilitate thrombolysis there. A high-power acoustic transducer 651 may be used to insonify and cavitate the thrombolytic bubbles 603 to accelerate the process.

Next, the localization of thrombolytic bubbles 603 and drug-induced or cavitation-induced thrombolysis may be repeated at the next location into the clot 604 until at least partial or complete revascularization is achieved.

Figure 7:
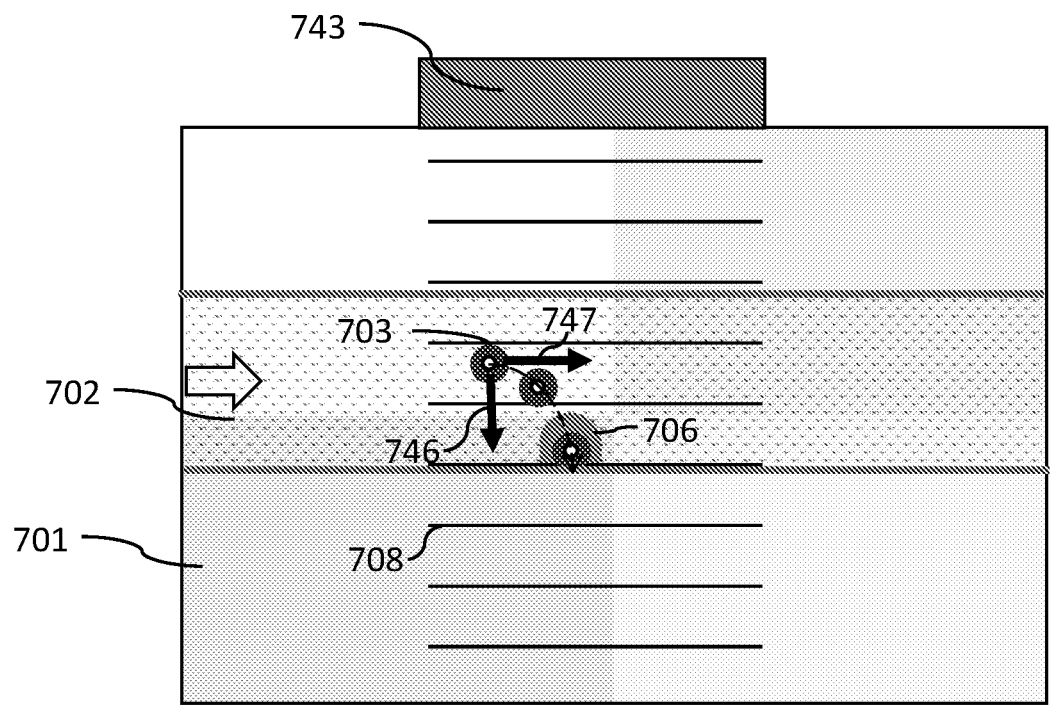
FIG. 7 is a diagram illustrating an aspect of the present disclosure using acoustic radiation force generated by an acoustic traveling wave to position a first structure that is used to form an internal, second structure.

According to another aspect of the present disclosure, as illustrated in FIG. 7, a first structure 703 (e.g. an acoustomotive bubble) may also be directed to an intended construction site 706 within a blood vessel 702, located inside a body 701. The first structure 703 may be directed by an acoustic traveling wave 708 generated by an extracorporeal positioning acoustic transducer 743. The acoustic traveling wave 708 may exert an acoustic radiation force 746 along the beam propagation direction. A flow-induced drag force 747 on the first structure 703 may be evaluated from the information about local flow speed obtained from an imaging apparatus. Therefore, the intensity of the acoustic wave 708 may be adjusted to direct the first structure 703 to the construction site 706 following a designed trajectory.

Figure 8:
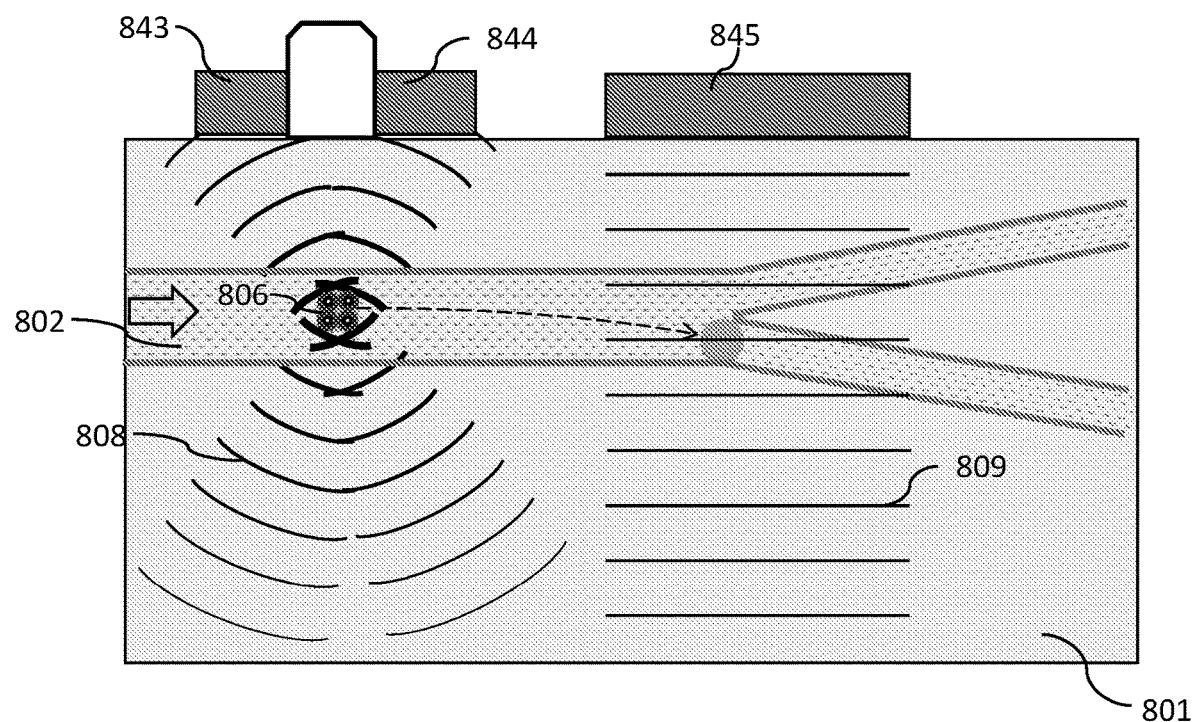
FIG. 8 is a diagram illustrating an aspect of the present disclosure, which forms a part of an internal structure at a first site, and subsequently drives it to a second site.

According to another aspect of the present disclosure, as illustrated in FIG. 8, a clot 806 may be first formed at a location that is different from a desired embolization site, and may be subsequently navigated to the desired site. Following steps similar to those described in relation to FIGS. 5A and 5B, a clot 806 may be formed inside a blood vessel 802 at a location in a body 801 that is not in the close proximity of a vessel wall. The clot 806 may be formed by trapping at least one first structure (e.g. hemostatic microbubbles) by an acoustic standing wave 808 generated by extracorporeal acoustic transducers 843, 844. Then, the clot 806 may be released from the trap, for example by turning off an acoustic standing wave 808. Next, the clot 806, may be navigated by, for example, a drag force provided by the blood flow, a gravity force, a buoyant force or an acoustic radiation force. The acoustic radiation force may be provided by an acoustic traveling wave 809 generated by another extracorporeal acoustic transducer 845. In certain situations, the acoustic standing wave 808 and the acoustic traveling wave 809 may also be generated by the same acoustic transducers.

Figure 9:
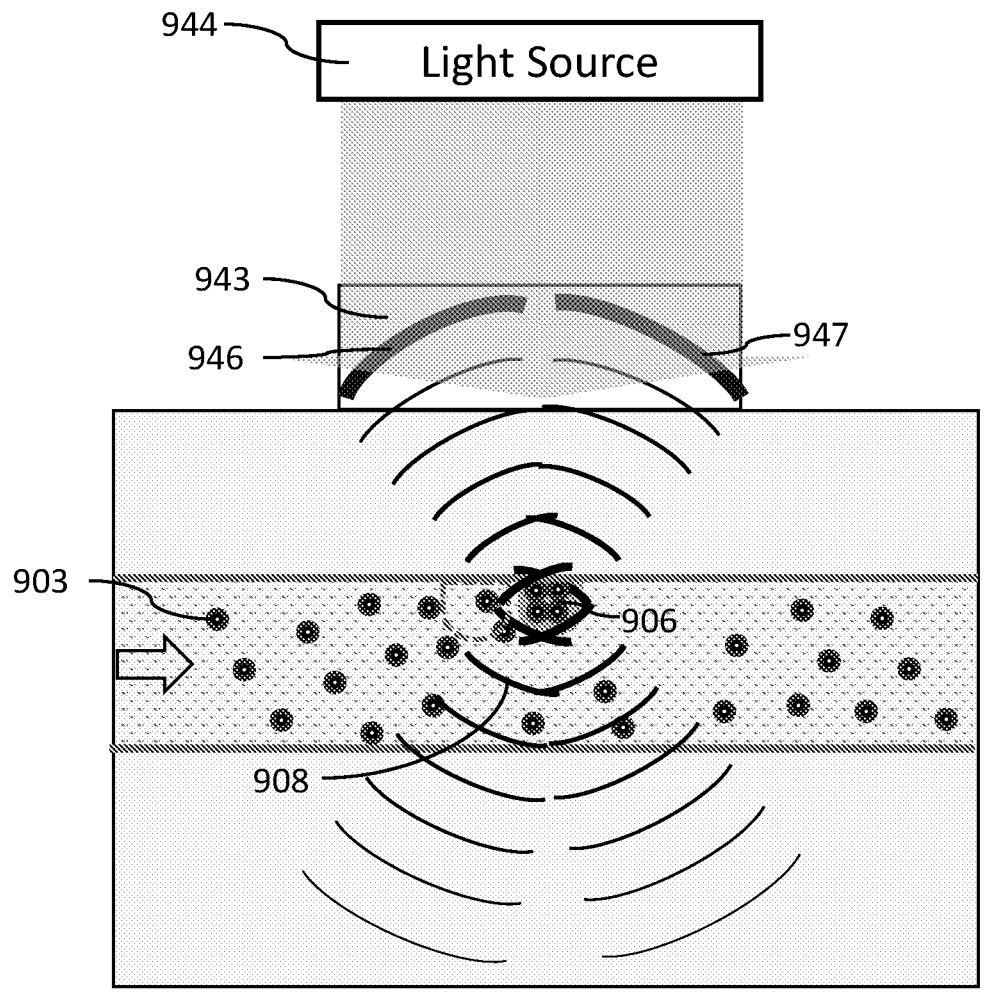
FIG. 9 is a diagram illustrating an aspect of the present disclosure using acoustic radiation force generated by a photoacoustic wave to position a first structure that is used to form an internal, second structure.

According to another aspect of the present disclosure, as illustrated in FIG. 9, an acoustic wave 908 for positioning first structures 903 (e.g. acoustomotive bubbles) at an intended construction site may be generated using a photoacoustic setup. The intended construction site may correspond to a desired blood clot 906. For example, a photoacoustic transducer 943 may contain optically absorbing inclusions 946, 947, which may emit acoustic wave under optical illumination generated by an light source 944 (e.g. a pulsed laser or an intensity-modulated continuous laser). The frequency of the resulting photoacoustic wave 908 may be tuned by varying the geometry of the absorbing inclusions 946, 947 or the modulation frequency of the light source 944. The intensity of the photoacoustic wave 908 may be adjusted by altering the output intensity of the light source 944 or the optical absorption properties of the absorbing inclusions 946, 947.

Finally, a desired pattern of the acoustic wave 908 may be achieved with using the absorbing inclusions 946, 947 with a specific geometry. Alternatively, the acoustic wave 908 may also be created by an exciting photoacoustic wave from intrinsic optical absorbing structures in the host object.

Figure 10A:
FIG. 10A is anon-limiting example of an intra-cavity implant—an intravascular stent—that may be constructed according to the present disclosure.
Figure 10B:
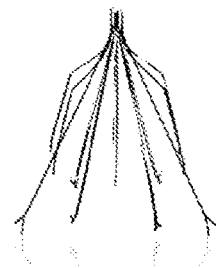
FIG. 10B is a non-limiting example of an intra-cavity implant—an inferior vena cava filter—that may be constructed according to the present disclosure.
Figure 10C:
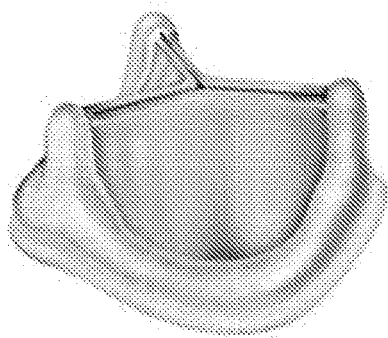
FIG. 10C is a non-limiting example of an intra-cavity implant—an artificial heart valve—that may be constructed according to the present disclosure.
Figure 10D:
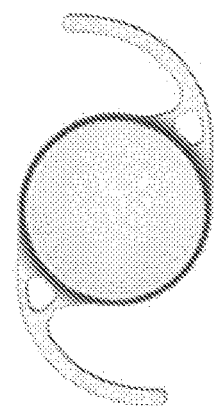
FIG. 10D is a non-limiting example of an intra-cavity implant—an intraocular lens—that may be constructed according to the present disclosure.
Figure 10E:
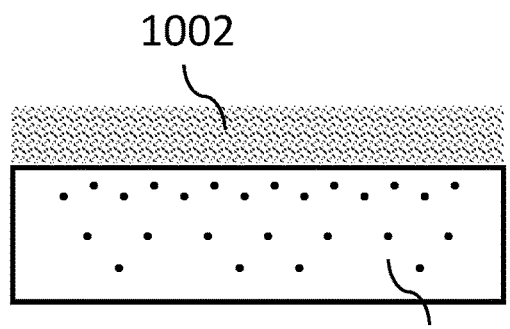
FIG. 10E is a non-limiting example of the creation of a drug-eluting attachment close to a focal lesion that may be constructed according to the present disclosure.
Figure 10F:
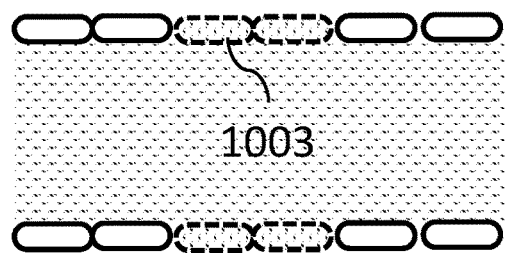
FIG. 10F is a non-limiting example of the repair of a damaged epithelium that may be performed according to the present disclosure.

Various aspects of the present disclosure may be used to perform different interventions noninvasively in a human body, without the need for open surgery or catheterization. As one non-limiting example, in the additive mode, various apparatuses according to the present disclosure may be used to introduce intra-cavity implants, such as an intravascular stent (as shown by FIG. 10A), an inferior vena cava filter (as shown by FIG. 10B), an artificial heart valve (as shown by FIG. 10C), and an artificial lens in an eye (as shown by FIG. 10D). In other non-limiting examples, various apparatuses according to the present disclosure may form a drug-eluting attachment 1002 in a close proximity of a focal lesion 1004 for long-term treatment (as shown by FIG. 10E), repair damaged epithelium by constructing a new one using introduced cells or therapeutic gene 1003 (as shown by FIG. 10F), or close perforated internal organs (e.g. luminal gastrointestinal tract).

In the subtractive mode, various apparatuses according to the present disclosure may be used, as non-limiting examples, to ablate cancer tissue, thrombus and atherosclerotic plaques. An apparatus according to the present disclosure may also work in a combined additive and subtractive mode to remove and replace a diseased tissue with a normal one or artificial implants.

Figure 11A:
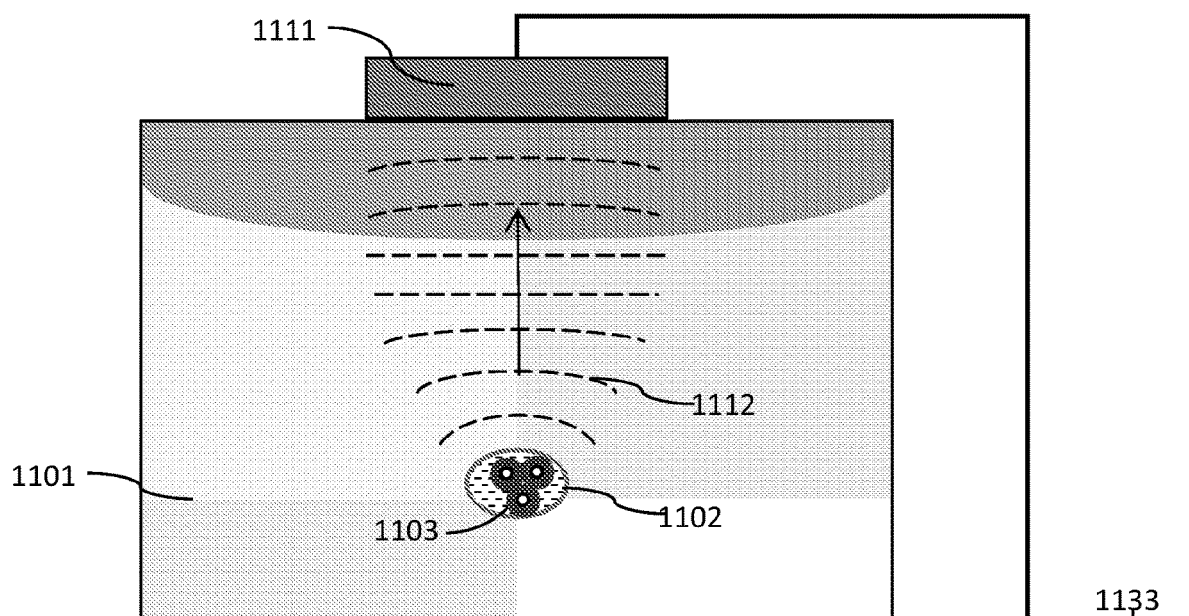
FIG. 11A is a diagram illustrating an aspect of the present disclosure, which uses a wave detection and modulation unit to compensate for wave distortion within a host object.
Figure 11B:
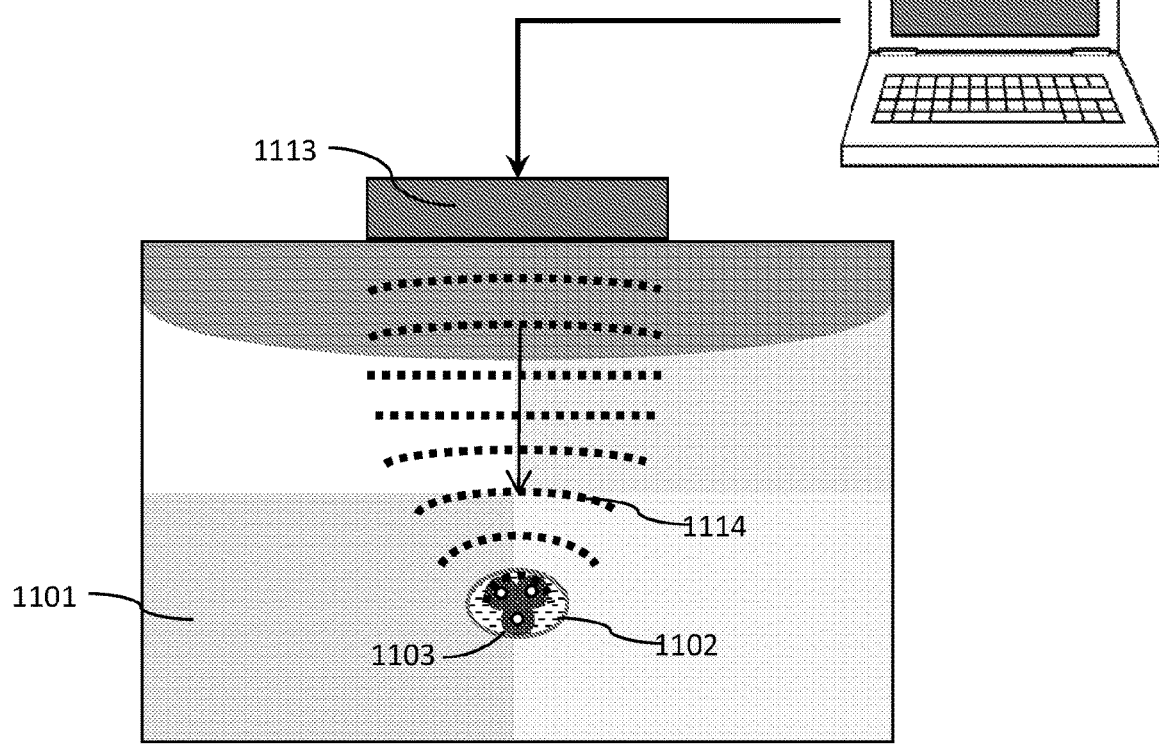
FIG. 11B is a diagram further illustrating the aspect of FIG. 11A in accordance with the present disclosure.

Another aspect according to the present disclosure may further comprise a wave detection and modulation unit. Heterogenous structures in a host object may distort a field, and may result in a sub-optimal field force on the at least one first structure at a target site. To address this problem, first, as illustrated in FIG. 11A, a detection unit 1111 may detect an acoustic wave 1112 reflected from or transmitted through a host object 1101 or a structure 1102 within the host object 1101. Then, as illustrated in FIG. 11B, a processing element 1133 may compute a correction factor, and direct the wave modulation unit 1113 to generate a wave-front correcting wave 1114. The wave-front correcting wave 1114 may be superimposed on a positioning field to compensate for the distortion within the object the 1101. Alternatively, the correction factor obtained by the processing element 1133 may be used to direct the positioning element to generate a corrected positioning field. The correction may allow sufficient force to be applied to the substances or agents 1103 to control their position or provide activation thereof.

FIGS. 12A-12C illustrate another aspect of the present disclosure, which may perform an intervention using acoustic radiation force in a hollow organ (e.g. an esophagus, a stomach, a small or large intestine, a cecum, a colon, a rectum, a bladder, a uterus, a vagina, a urethra, a trachea or a lung) or a cavity (e.g. an abdominal cavity) 1202. As illustrated in FIG. 12A, to reduce the acoustic reflection at a tissue-air interface, an acoustic coupling agent 1210 may be introduced into the hollow organ or cavity 1202 through swallowing, injection, or infusion. The acoustic coupling agent 1210 may further contain at least one acoustomotive first structure 1203. A positioning acoustic apparatus 1243 may generate an acoustic wave 1208, which may propagate towards the hollow organ or cavity 1202. As the coupling agent reaches the targeted site and increases the local sound transmission, the acoustic wave 1208 may penetrate into the hollow organ or cavity 1202 and position at least one of the acoustomotive first structures 1203 there. Then, the first structures 1203 may interact with each other, with native material inside the host object 1201, or with material in the coupling agent 1210. The interaction may create an internal structure 1206 (shown in FIG. 12B) or remove a piece of tissue 1207 (shown in FIG. 12C) at the targeted site. This device may be used to perform various interventions inside a hollow organ or cavity, such as repairing a perforated wall, removing a tumor, and ablating Barrett's esophagus. For the avoidance of doubt, aspects of the present disclosure described with respect to the systems are applicable to the methods and aspects described with respect to the methods are applicable to the systems.

The foregoing merely illustrates the principles of the disclosure. Various modifications and alterations to the described aspects will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. Further, the exemplary aspects described herein can operate together with one another and interchangeably therewith. In addition, to the extent that the prior art knowledge has not been explicitly incorporated by reference herein above, it is explicitly being incorporated herein in its entirety. All publications referenced herein above are incorporated herein by reference in their entireties.

We claim:

1. A method for utilizing a plurality of first structures containing a material at a target site inside or adjacent to a host object, comprising:
    a) using an external source to generate a first field that non-invasively penetrates into the host object;
    b) using the first field to directly position a first portion of the plurality of first structures at the target site,
        wherein the first field comprises an acoustic field,
        wherein the plurality of first structures comprises at least one of hemostatic bubbles, thrombolytic bubbles, or acoustomotive bubbles, and
        wherein the first portion of the plurality of first structures is positioned at the target site using the acoustic field;
    c) optionally generating a second field that non-invasively penetrates into the host object;
    d) releasing the material from the plurality of first structures, wherein the releasing is initiated by the first field or the second field; and e) at least one of:
  forming, based on interactions between the materials released from the plurality of first structures, a second structure comprising the released material inside or adjacent to the host object, or
  removing, based on interactions between the materials released from the plurality of first structures, a third structure comprising the released material inside or adjacent to the host object and at least a portion of the host object.

2. The method according to claim 1, the releasing of step d) thereby forming the second structure from the material inside or adjacent to the host object, wherein the interactions between the released materials are caused by at least one of a chemical bond, a magnetic force, an acoustic force, heat, or an electrostatic force.

3. The method according to claim 2, wherein the forming the second structure thereby inhibits a blood flow inside or adjacent to the host object via the second structure.

4. The method according to claim 2, wherein the second structure: i) applies a mechanical force on a vessel wall to maintain patency of a lumen; ii) has a different size and/or shape from the plurality of first structures; iii) blocks blood flow; iv) includes an intra-cavity implant; v) creates at least one blood clot; vi) is configured to lyse a blood clot; or vii) any combination thereof.

5. The method according to claim 1, the releasing of step d) thereby removing the third structure from inside or adjacent to the host object based on the interactions between the released materials.

6. The method according to claim 5, wherein the removing of the third structure thereby enhances a blood flow inside or adjacent to the host object.

7. The method according to claim 1, wherein the release of the material causes a reaction of polymerization, chemical cross-linking, or activation of a cascade in the host object.

8. The method according to claim 1, further comprising imaging the target site to determine a desired position of the first portion of the plurality of first structures, prior to step a).

9. The method according to claim 1, wherein the acoustic field includes a standing wave and the target site is located at one of a standing wave node or a standing wave antinode.

10. The method according to claim 1, wherein the host object is an object within a human body.

11. A system for utilizing a plurality of first structures containing a material at a target site inside or adjacent to a host object, the system comprising:
  a first field generator configured to generate a first field that propagates into the host object and directly exerts a force on at least one of the plurality of first structures;
  a first field generator controller configured to direct the first field generator to generate the first field following a specific pattern that positions at least one of the plurality of first structures at the target site to form a second structure comprising the material inside or adjacent to the host object,
  wherein the first field comprises an acoustic field,
  wherein the plurality of first structures comprises at least one of hemostatic bubbles, thrombolytic bubbles, or acoustomotive bubbles, and
  wherein the at least one of the plurality of first structures is positioned at the target site using the acoustic field; and
  optionally a second field generator controller and optionally a second field generator, wherein the first field generator controller or the second field generator controller is configured to direct the first field generator or the second field generator to exert a second field that releases the material from the at least one of the plurality of first structures at the target site,
  wherein the second structure is formed based on interactions between the materials released from the plurality of first structures, and
  wherein the second structure comprises the released materials.

12. The system according to claim 11, the system comprising the second field generator controller and the second field generator, wherein the second field generator controller is configured to direct the second field generator to exert the second field that released the material from the at least one of the plurality of first structures at the target site.

13. The system according to claim 11, further comprising at least one of a syringe, a material injector, an infusion pump, or an intravenous catheter configured to introduce the plurality of first structures containing the material into or adjacent to the host object.

14. The system according to claim 11, further comprising an imaging device configured to image inside or adjacent to the host object.

15. A field-deployable kit comprising:
  a plurality of first structures containing a material, and configured for insertion near a target site within or adjacent to a host object;
  a field generator including a power supply; and
  a non-transient computer readable medium containing program instructions for causing a computer to perform a method of:
    a) generating, using the field generator, a field configured to directly drive the plurality of first structures from an injection site to the target site,
  wherein the field comprises an acoustic field,
  wherein the plurality of first structures comprises at least one of hemostatic bubbles, thrombolytic bubbles, or acoustomotive bubbles,
  wherein the plurality of first structures are driven to the target site using the acoustic field,
  wherein the plurality of first structures are configured to release the material from the plurality of first structures, wherein the release is initiated by the field or a second field generated by the field generator or a second field generator, and
  wherein a second structure comprising the released material is formed within or adjacent to the host object based on interactions between the materials released from the plurality of first structures.

* * * * *

UNITED STATES PATENT AND TRADEMARK OFFICE
CERTIFICATE OF CORRECTION

| | | |
|---|---|---|
| PATENT NO. | : 11,801,374 B2 | Page 1 of 1 |
| APPLICATION NO. | : 16/329862 | |
| DATED | : October 31, 2023 | |
| INVENTOR(S) | : Li Li et al. | |

It is certified that error appears in the above-identified patent and that said Letters Patent is hereby corrected as shown below:

In the Specification

Column 4, Line 22, "anon-limiting" should be --a non-limiting--.

Signed and Sealed this
Second Day of January, 2024

Katherine Kelly Vidal
*Director of the United States Patent and Trademark Office*